United States Patent [19]

Drakulic

[11] Patent Number: 5,678,559

[45] Date of Patent: Oct. 21, 1997

[54] EEG SYSTEM

[76] Inventor: Budimir S. Drakulic, 10751 Wilshire Blvd.-PH.9, Los Angeles, Calif. 90024

[21] Appl. No.: 376,405

[22] Filed: Jan. 23, 1995

[51] Int. Cl.$^6$ .................................................. A61B 5/0476
[52] U.S. Cl. ........................ 128/731; 128/901; 128/902
[58] Field of Search ................................. 123/731, 734, 123/745, 639, 644, 901, 902, 908, 696; 607/139; 364/413.05

[56] References Cited

U.S. PATENT DOCUMENTS

| | | | |
|---|---|---|---|
| 4,201,224 | 5/1980 | John | 128/731 |
| 4,204,546 | 5/1980 | Smith et al. | 128/731 |
| 4,928,704 | 5/1990 | Hardt | 128/732 |
| 5,038,782 | 8/1991 | Gevins et al. | 128/731 |
| 5,273,037 | 12/1993 | Itil et al. | 128/731 |
| 5,368,041 | 11/1994 | Shambroom | 128/731 |

*Primary Examiner*—Jeffrey R. Jastrzab
*Attorney, Agent, or Firm*—Ellsworth R. Roston

[57] ABSTRACT

Electrodes, preferably paired on a patient's head, produce signals representing the patient's brain waves at one of the paired electrodes and reference signals at the other paired electrode. Pre-amplifiers juxtaposed to the paired electrodes and having a balanced operation even with impedance differences between the paired electrodes produce signals representing the difference in the signals between such electrodes. After filtering to eliminate DC and band limit the upper frequency, the signals from each pre-amplifier pass to a post-amplifier displaced and electrically isolated from the pre-amplifier. The post-amplifier linearly amplifies the pre-amplifier signals and filters the signals at the lower and upper frequencies within a particular frequency range dependent upon the frequency range in which the investigator is interested. The upper and lower limits of the frequency range are dependent upon the frequencies of controlling clock signals. The upper and lower clock frequencies may be varied progressively to determine the characteristics of the signals produced at the individual ones of the electrodes from brain wave shapes at such electrodes. The cut-off characteristics of the pre-amplifier at the upper and lower frequency limits may be varied by adjusting impedance values in the filter. An electroocular system constructed similarly to, and operative in timed relationship with, the electrode encephalographic system indicates whether signals at the electroencephalographic electrodes result from the patient's eye movements. An electrocardiographic system constructed similarly to, and operative in timed relationship with, the electroencephalographic system indicates the relationship between the patient's brain and heart waveforms.

52 Claims, 11 Drawing Sheets

FIG. 5
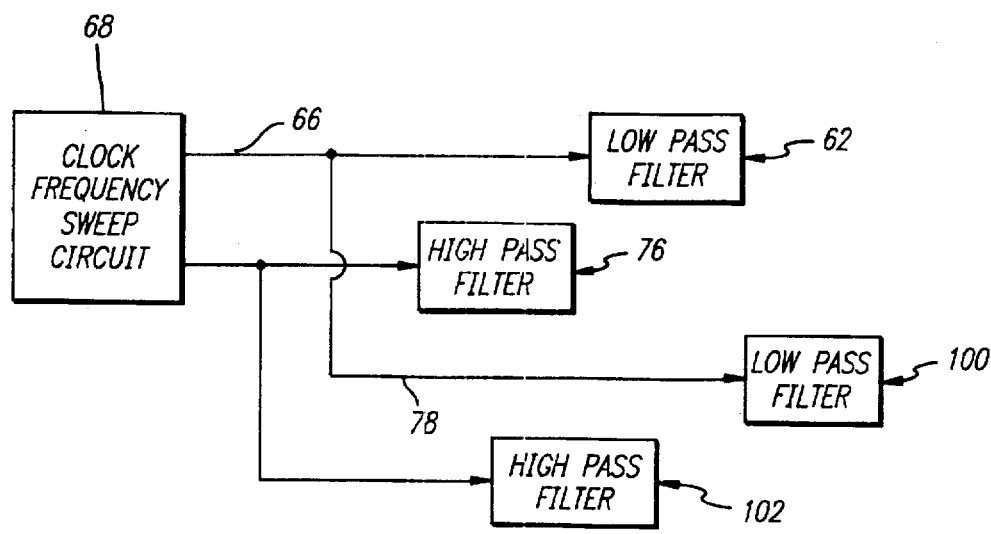
FIG. 6
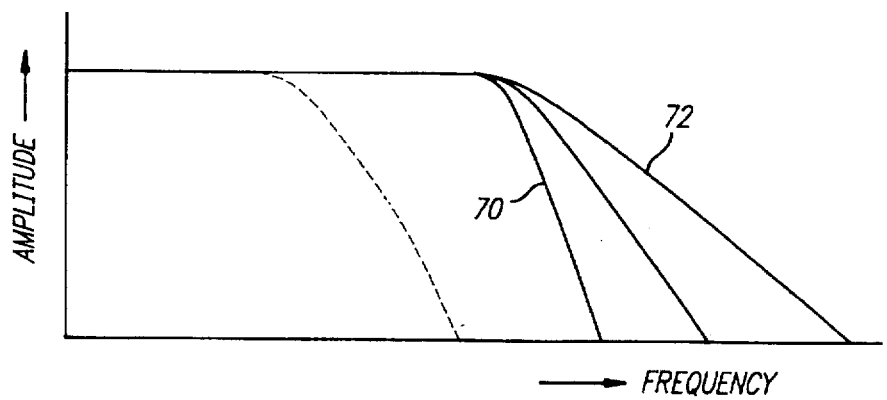
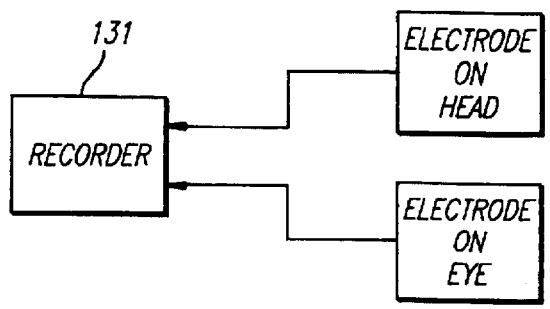
FIG. 8

| FIG. 7(A) | FIG. 7(B) | FIG. 7(C) |

EEG SYSTEM

This method relates to systems for, and methods of, producing electroencephalograms of a patient's brain. The system and method of this invention can be generalized for use to provide electroocular information and electrocardiographic information.

BACKGROUND OF THE INVENTION

It has been discovered in recent years that a significant percentage of people have sleep problems. These problems may result from a number of different causes. For example, such sleep problems may result from physical defects in the nose of a person or from involuntary movements of different parts of the body such as a person's arms or legs. Such physical defects or such involuntary movements of a person's arms or legs may cause the person to awaken subconsciously, thereby breaking the person's sleep patterns. Since these involuntary actions can occur to a person many times during a night, such person awakens in the morning incompletely refreshed.

Progress has been made over a period of at least twenty (20) years in determining the reasons why a person complains of insufficient sleep. For example, electrodes have been attached to a person's head to record signals representing brain waves at different locations in the person's brain. Electrodes have also been attached to different positions (e.g. legs of a person's body) to produce signals indicating whether or not the patterns of signals produced at such different positions on the person's body as a result of movements of the patient's body at such positions are correlated with the signals produced at the electrodes on the person's head to indicate the brain waves at such electrodes. The signals produced at the different electrodes are then analyzed to determine the reasons why such person has insufficient sleep.

Although considerable progress has been made in recent years to determine why a person has insufficient sleep, significant problems still remain. One of the major problems is that the signals produced at the different electrodes on the head are quite weak. This has made it difficult, and sometimes impossible, to obtain meaningful information from the signals at different electrodes even when such electrodes are attached to a person's head and signals are produced at such electrodes and are recorded for subsequent analysis. Another reason has been that the equipment associated with such electrodes is quite bulky and cumbersome and, even though bulky and cumbersome, is still unable sometimes to provide meaningful information.

A third problem has been that, at least partially as a result of the bulky and cumbersome equipment attached to the electrodes, the person undergoing examination is not ambulatory after the electrodes have been attached to such person. This has restricted the movements of such person, particularly while such person is sleeping. If anything, the confinement of such person against movement has inhibited such movement from sleeping properly. This has tended to qualify the legitimacy of the tests performed on such person.

As will be seen, although much progress has been made in recent years to determine the reasons for insomnia, or at least insufficient sleep, in people, much progress still remains to be accomplished. For example, it would be desirable to provide equipment which always provides accurate and meaningful information for subsequent analysis. Furthermore, it would be desirable for persons to be ambulatory, much as is now accomplished with heart monitors which have the size and weight of a light purse and thus are easily carried by persons for a period of twenty four (24) hours. In this way, persons can sleep in their beds at home to enhance the meaningfulness of the tests and to minimize any inconvenience to such persons.

BRIEF DESCRIPTION OF THE INVENTION

This invention provides a system which accomplishes the desirable features discussed above. The system provides sensitive and reliable measurements of the signals produced at the electrodes on a person's head in representation of the brain waves at such electrodes. The system is so light and small that the patient can be ambulatory. The system is so inexpensive that a person of relatively modest means can afford the costs of tests to determine the reasons for such person's insomnia or relative lack of sleep.

In one embodiment of the invention, electrodes, preferably paired on a person's head, produce signals representing the person's brain waves at one of the paired electrodes and reference signals at the other paired electrode. Pre-amplifiers juxtaposed to the paired electrodes and having a balanced operation even with impedance differences between the paired electrodes produce signals representing the difference in the signals between such electrodes.

After filtering to eliminate DC and band limit the upper frequency, the signals from each pre-amplifier pass to a post-amplifier displaced and electrically isolated from the pre-amplifier. The post-amplifier linearly amplifies the pre-amplifier signal and filters the signals at the lower and upper frequencies within a particular frequency range dependent upon the frequency range in which the investigator is interested.

The upper and lower limits of the frequency range are dependent upon the frequencies of controlling clock signals. The upper and lower clock frequencies may be varied progressively to determine the characteristics of the signals produced at the individual ones of the electrodes from brain waveshapes at such electrodes. The cut-off characteristics of the post-amplifier at the lower and upper frequency limits may be varied by adjusting impedance values in the filter.

An electrocular system constructed similarly to, and operative in timed relationship with, the electrode encephalographic system indicates whether signals at the electroencephalographic electrodes result from the person's eye movements. An electrocardiographic system constructed similarly to, and operative in timed relationship with, the electro-encephalographic system indicates the relationship between the patient's brain and heart waveforms.

BRIEF DESCRIPTION OF THE DRAWINGS

In the drawings:

FIG. 4 is a map showing the relative dispositions of FIGS. 4A–4D;

3

Figure 3:
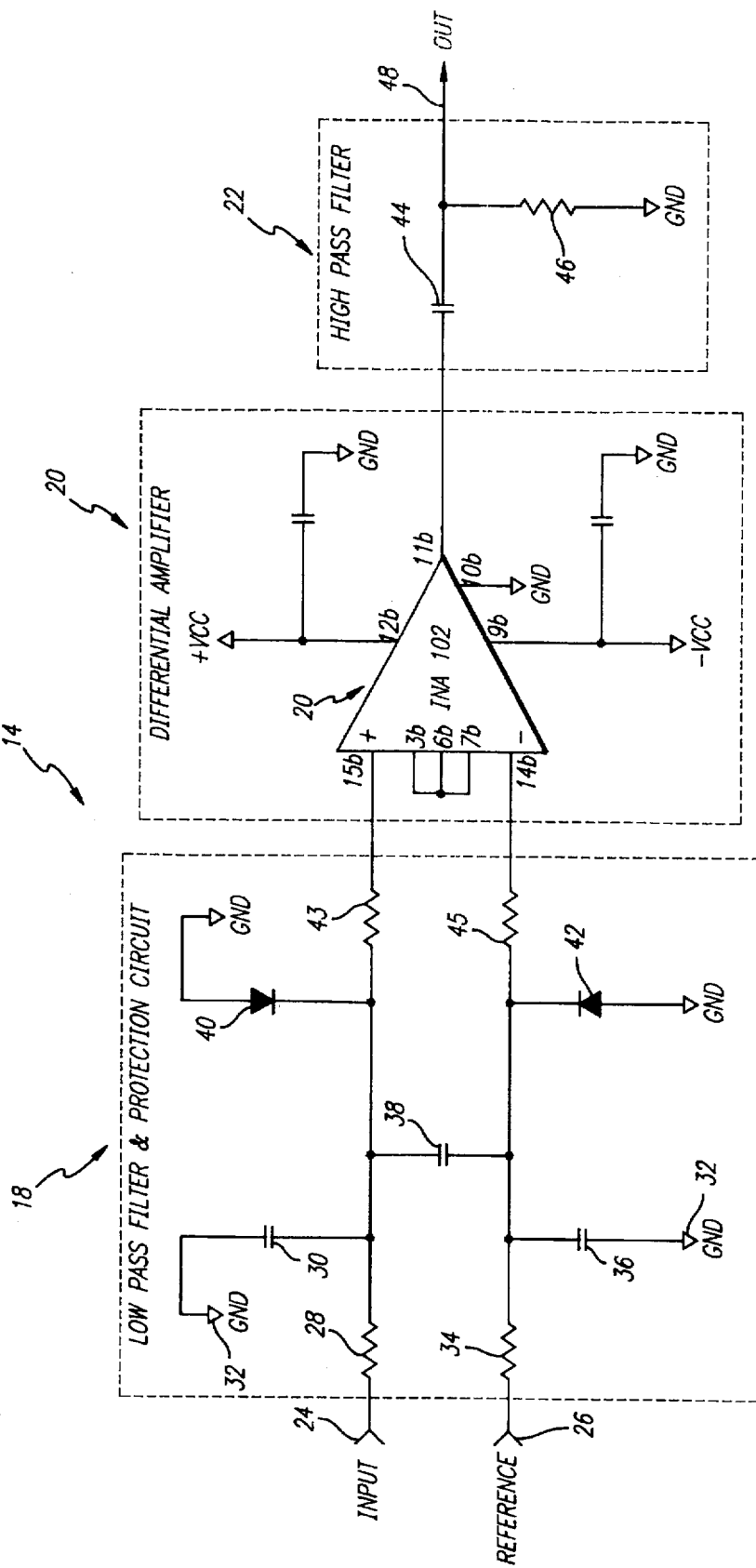
FIG. 3 is a circuit diagram, partially in block form, of the electrical circuitry included in one of the pre-amplifiers.
Figure 4A:
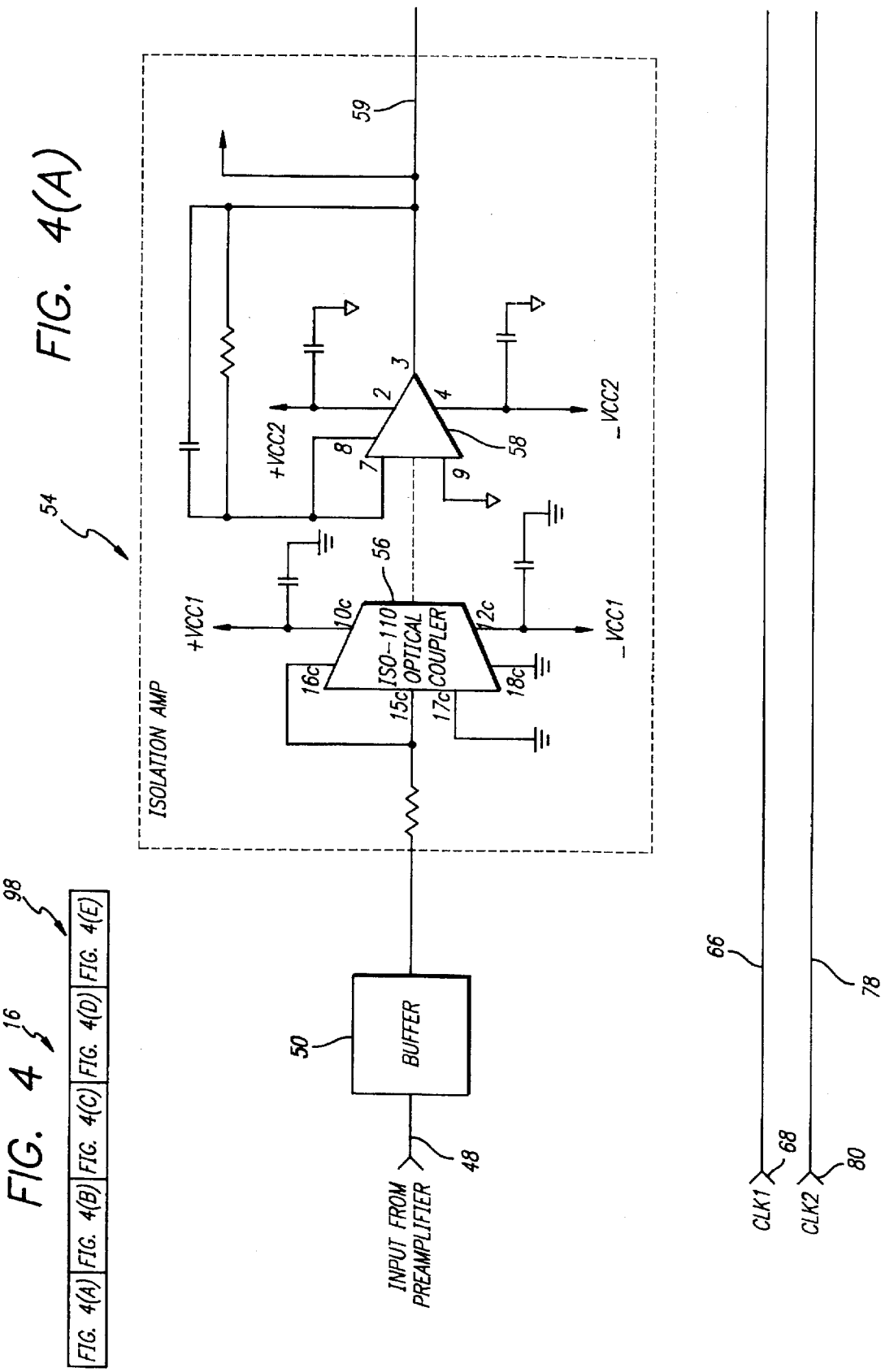
FIGS. 4A, 4B, 4C and 4D collectively show a circuit diagram, partially in block form, of the electrical circuitry included in a pair of the post amplifiers.
Figure 4B:
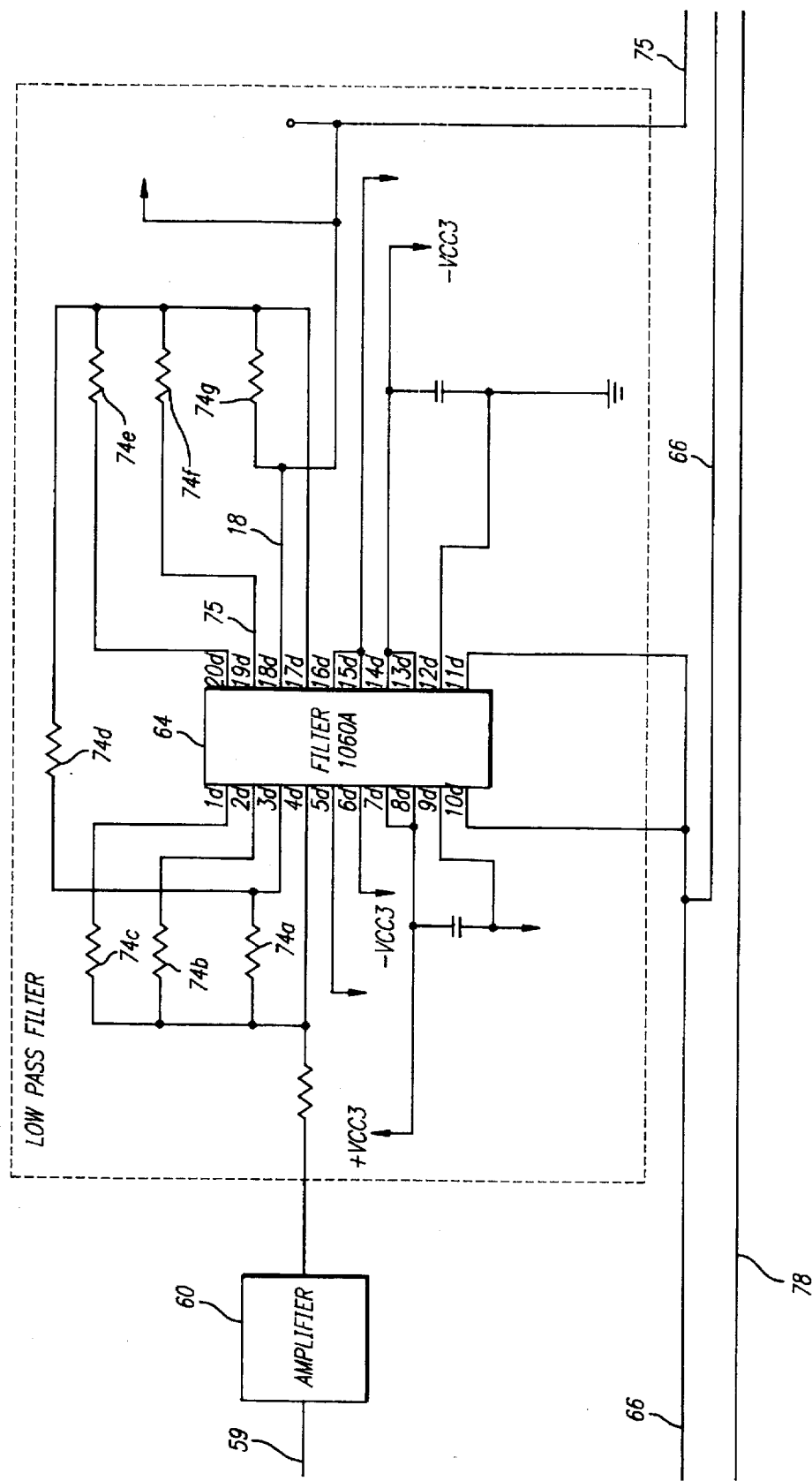
Figure 4C:
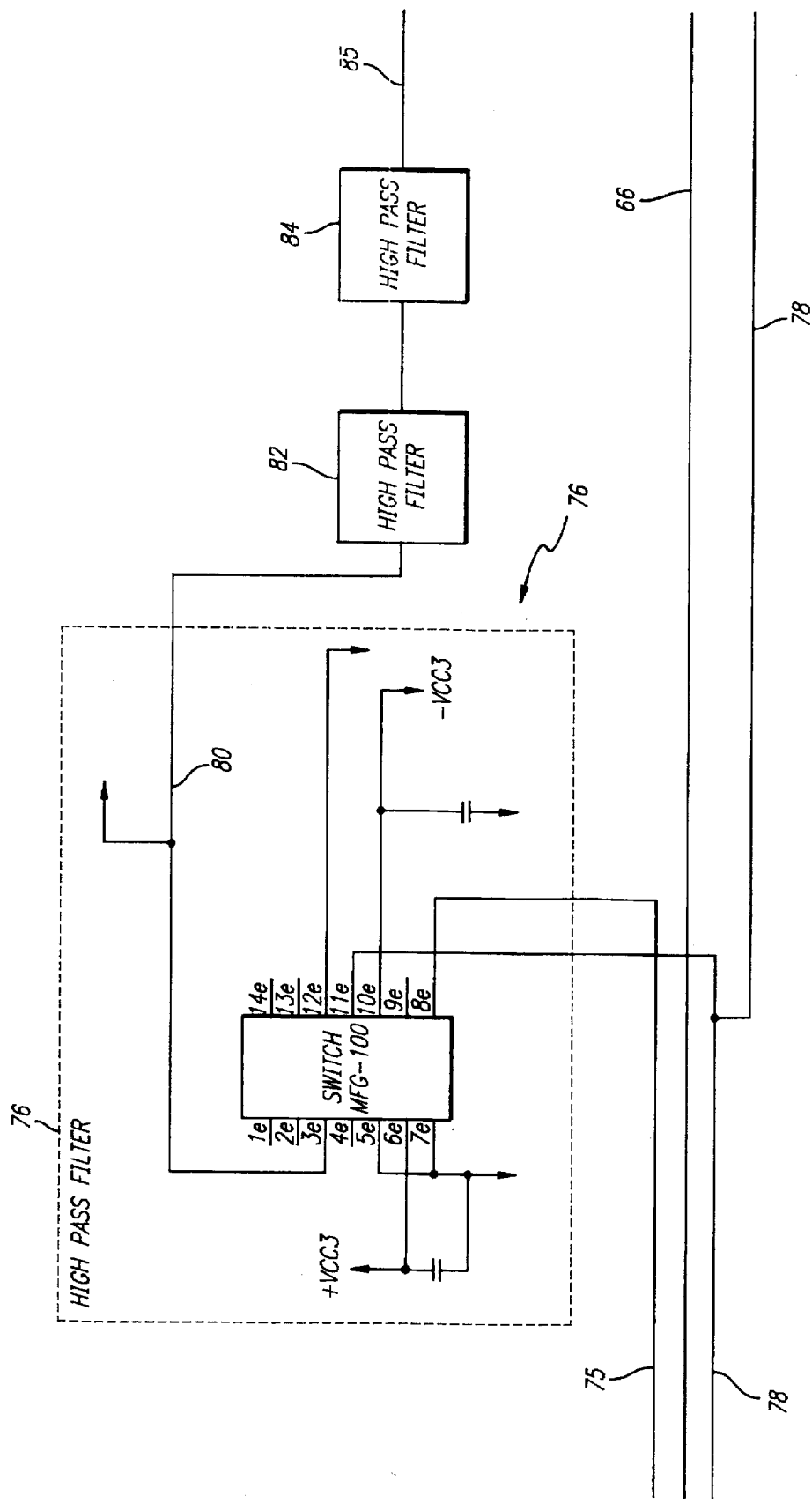
Figure 4D:
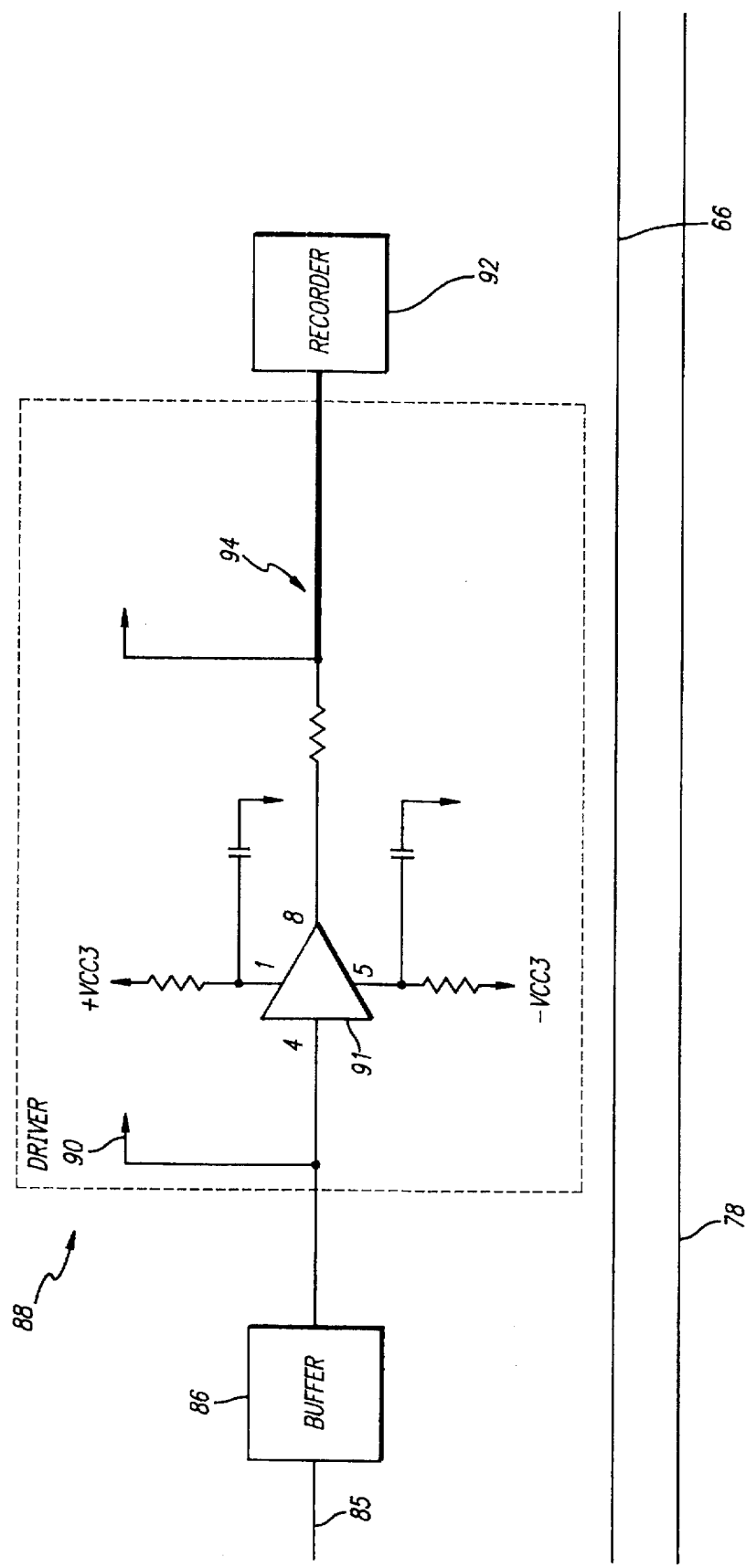
Figure 4E:
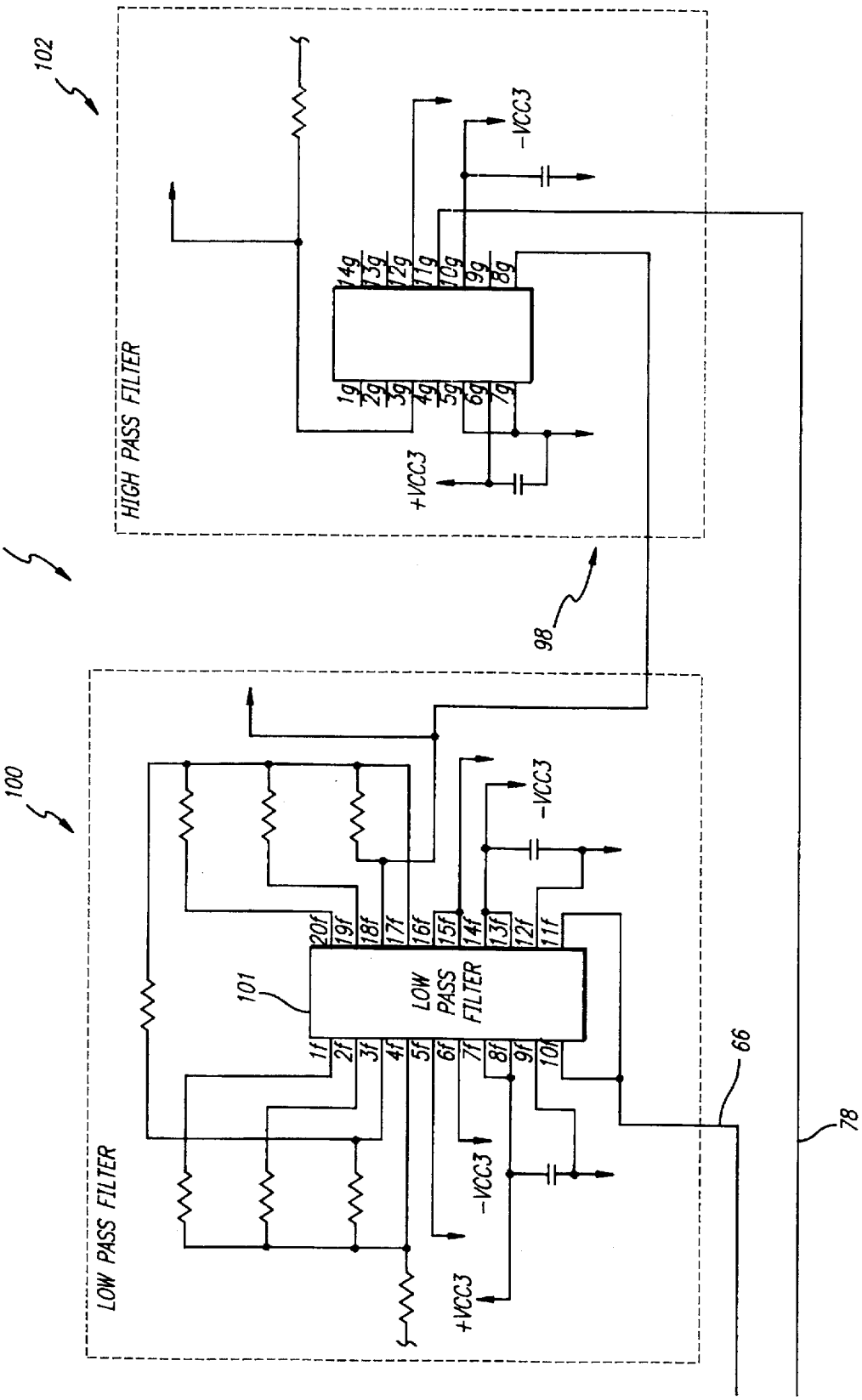
FIG. 4E shows strategic portions of another post-amplifier similar to the post-amplifier shown collectively in FIGS. 4A–4D.
Figure 7A:
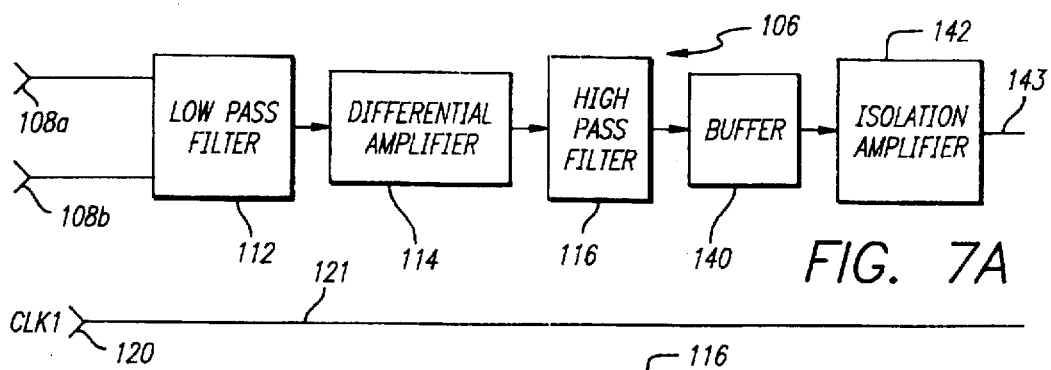
Figure 7G:
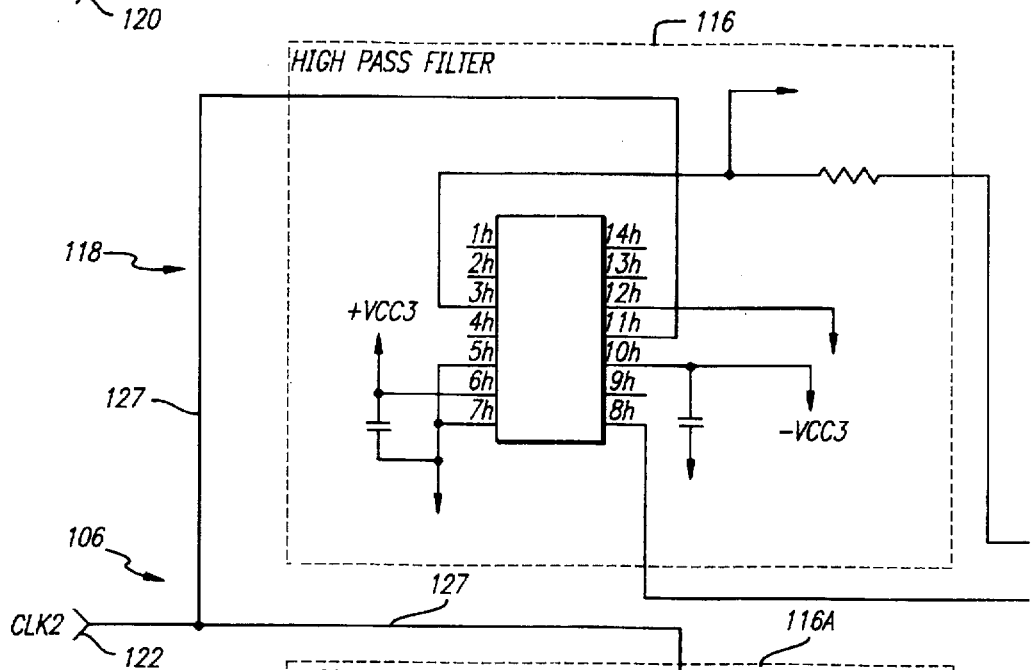
Figure 7D:
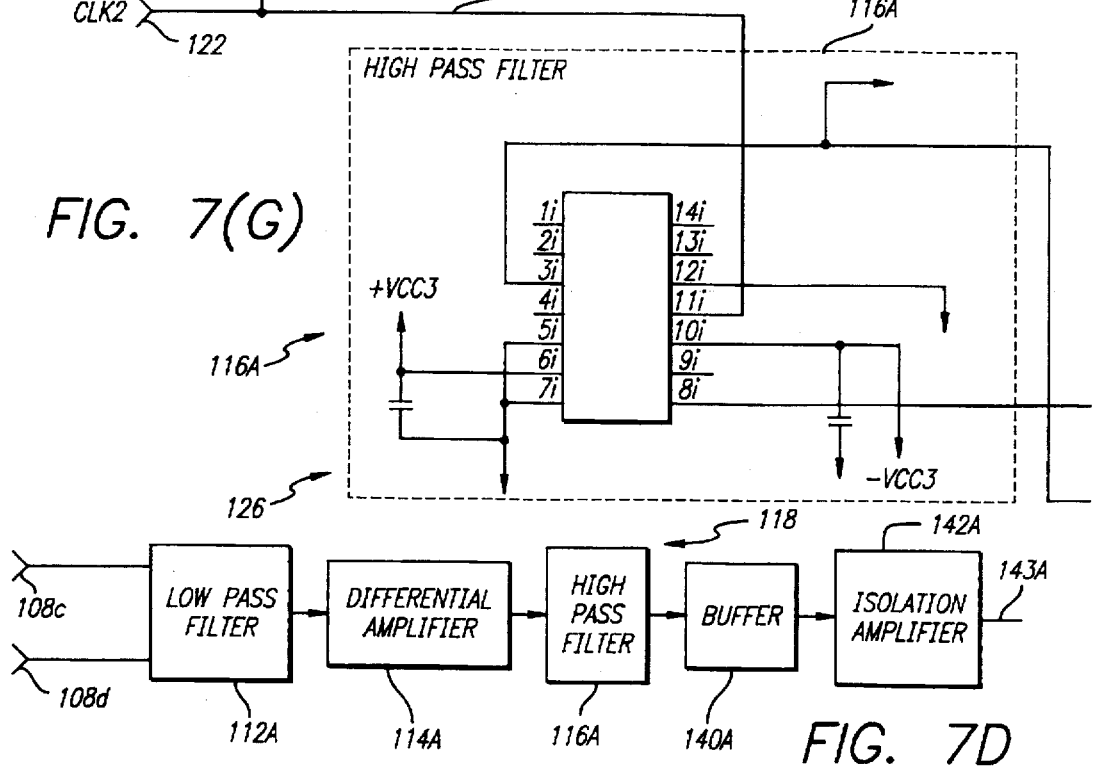
Figure 7F:
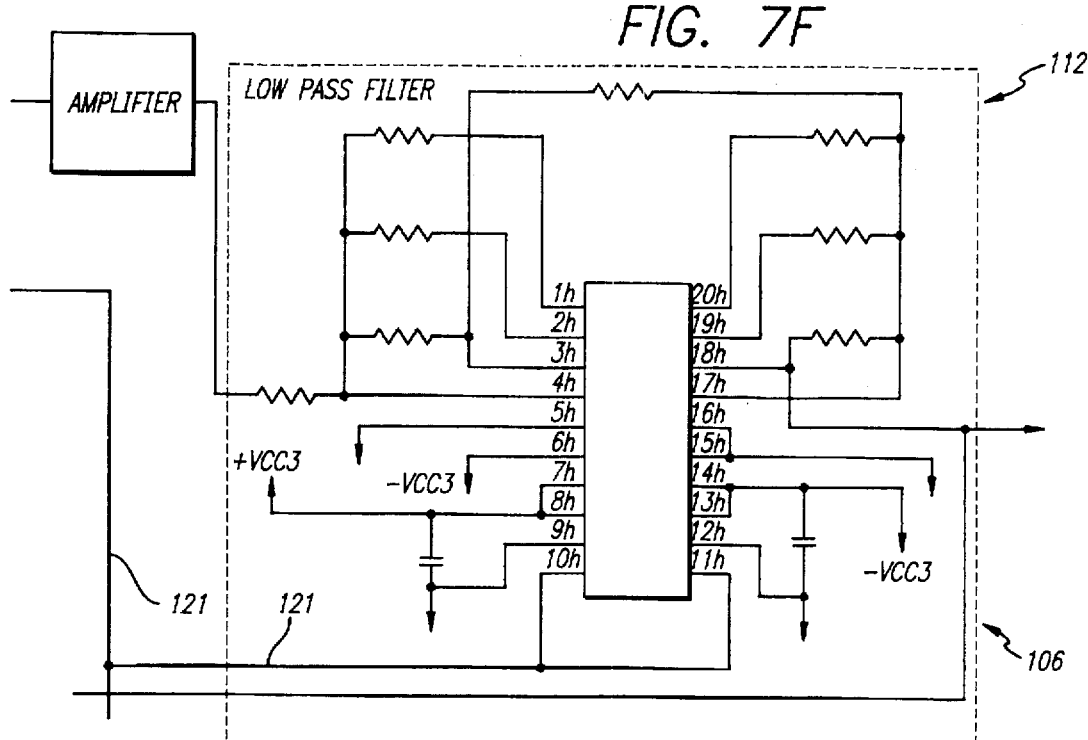
Figure 7B:
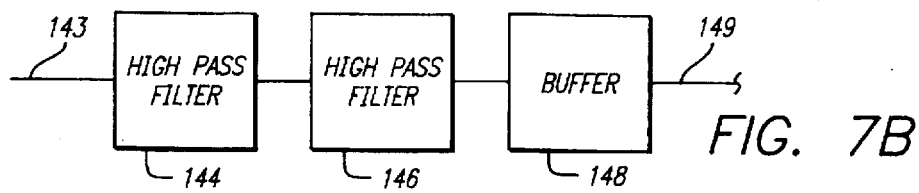
Figure 7E:
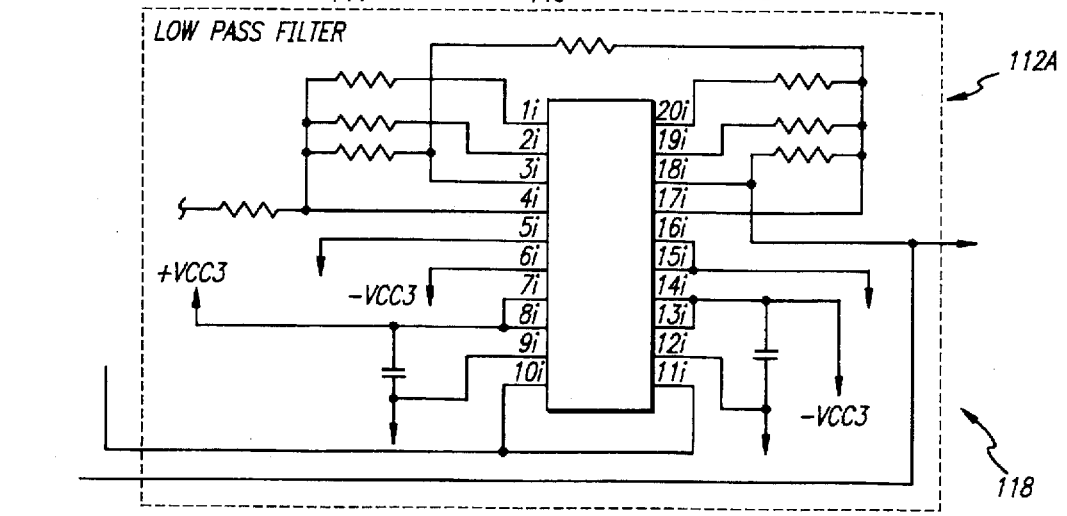
Figure 7E:
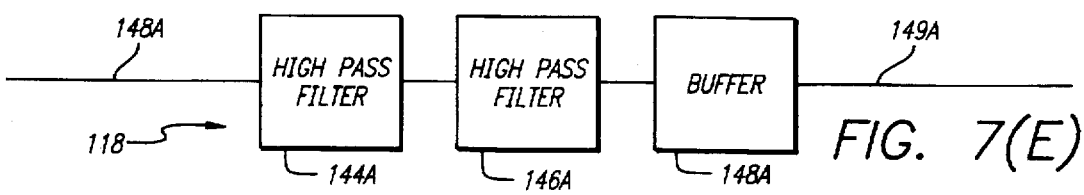
Figures 7, 7C:
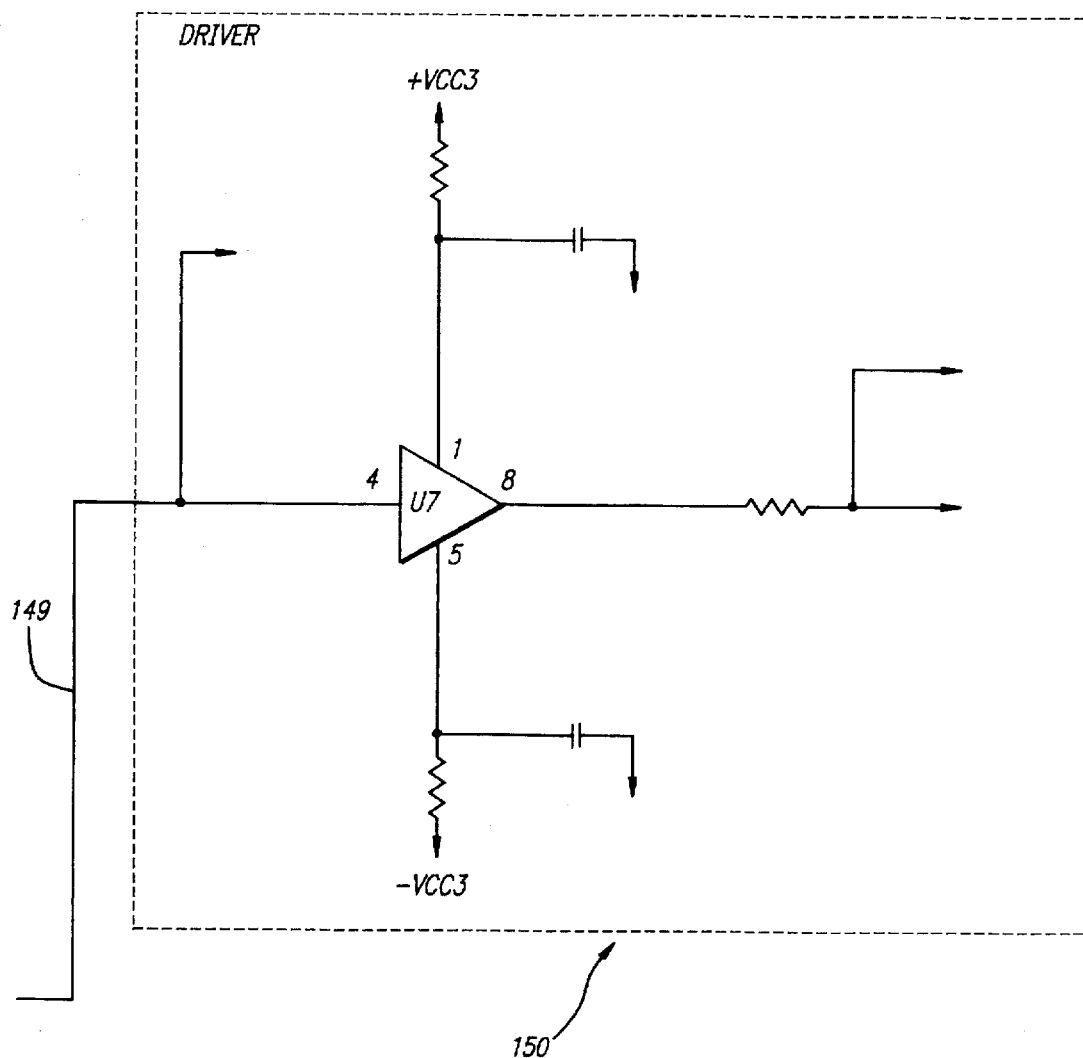

FIG. 5 is a circuit diagram illustrating how the circuitry shown in FIGS. 4A–4D and in FIG. 4E can be employed to determine the characteristics of the signals at different ones of the electrodes;

FIG. 6 shows curves illustrating the different frequency responses of the signals at individual ones of the electrodes and the cut-off characteristics which can be provided in the signals produced by the circuitry shown in FIGS. 3 and 4;

FIG. 7 is a map showing the relative dispositions of FIGS. 7A–7C;

FIGS. 7A, 7B and 7C collectively show a circuit diagram of a post-amplifier, similar to that shown in FIG. 4, which may be used in a system for measuring the movements of the patient's eyes or for measuring the characteristics of the signals produced in the patient's heart;

FIG. 7D and 7E collectively show a circuit diagram of a post-amplifier similar to that shown in FIGS. 7A–7C;

FIG. 7F is a circuit diagram of a low pass filter included in the post-amplifiers shown in FIGS. 7A–7C and 7D–7E and corresponding to a low pass filter shown in FIG. 4B;

FIG. 7G is a circuit diagram of a high pass filter included in the post-amplifier shown in FIGS. 7A–7C and 7D–7E and corresponding to a high pass filter shown in FIG. 4C; and FIG. 8 is a schematic diagram of signals produced in a timed relationship by the combination of the pre-amplifier shown in FIG. 3 and the post amplifier shown in FIG. 4 and by the circuitry shown in FIG. 7.

DETAILED DESCRIPTION OF THE INVENTION

Figure 1:
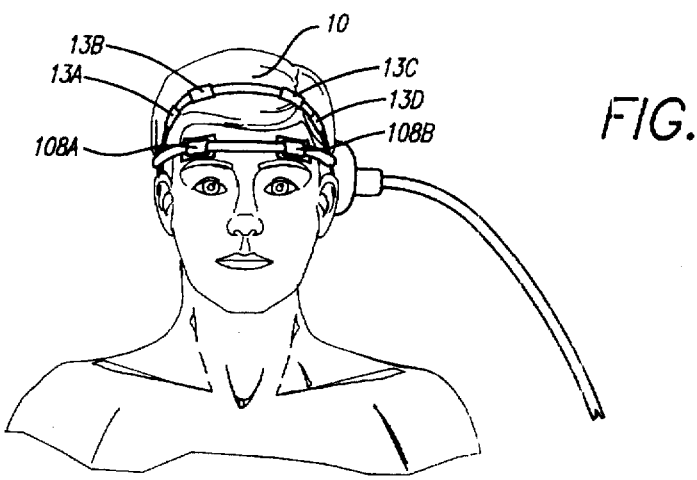
FIG. 1 is a schematic view of a plurality of a plurality of electrodes on a patient's head.

FIG. 1 is a schematic diagram of a patient's head 10 and of electrodes 12A, 12B, 12C, 12D, etc. disposed on the patient's head to produce signals having characteristics corresponding to the characteristics of the brain waves produced at such electrodes. The electrodes may be attached to the patient's head in a manner well known in the art. The positions of the electrodes 12A, 12B, 12C, etc. on the patient's head are carefully chosen because each position provides individual information which may be different from the information at the positions of other electrodes.

Figure 2:
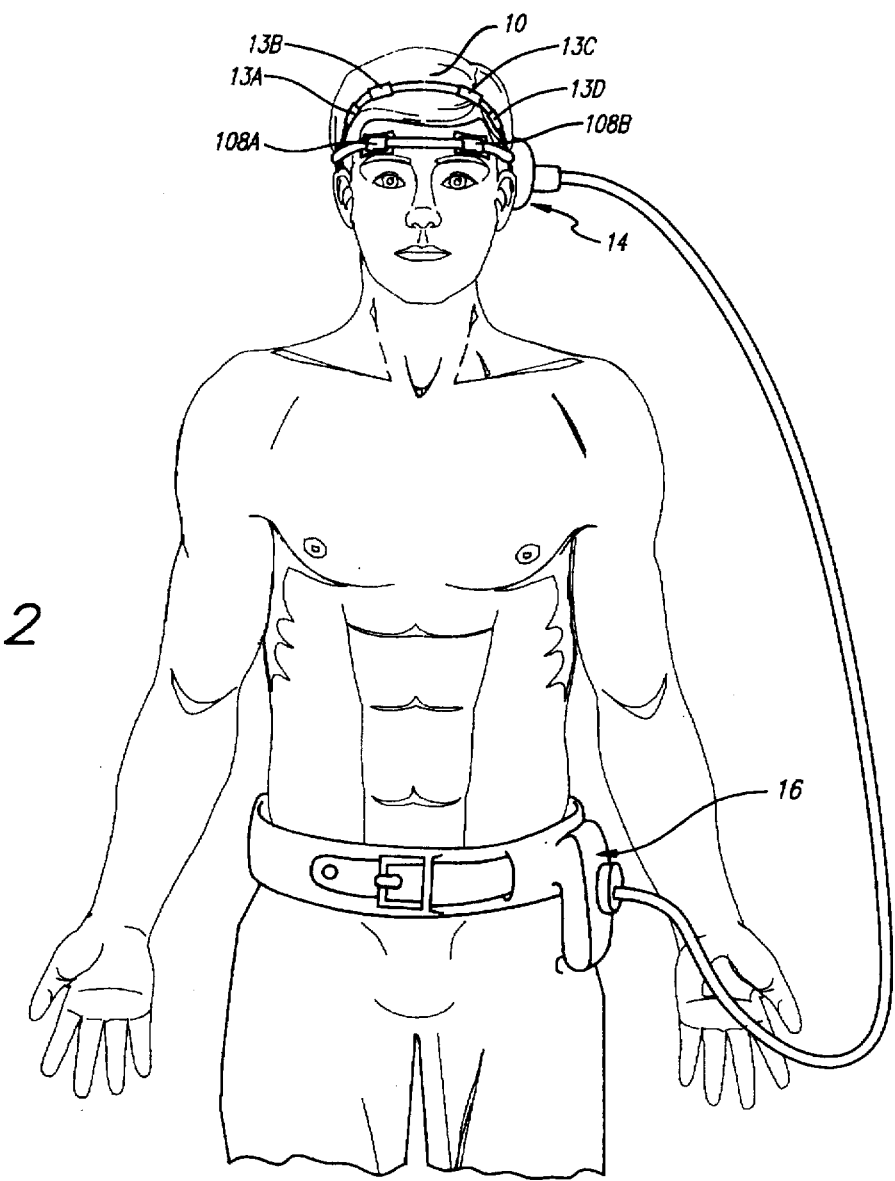
FIG. 2 is a schematic view similar to that shown in FIG. 1 but shows the position relative to the electrodes of pre-amplifiers and post-amplifiers which operate upon the signals from the electrodes.

FIG. 2 shows the disposition of a pre-amplifier generally indicated at 14 and of a post-amplifier, generally indicated at 16, relative to the electrodes 12A, 12B, 12C, 12D, etc. The circuitry of the pre-amplifier 14 is shown in detail, but partially in block form, in FIG. 3 and the circuitry of the post amplifier 16 is shown, partially in block form, in detail in FIG. 4. As will be seen, the pre-amplifier 14 in FIG. 2 is disposed in juxtaposition to the patient's head. The reason for this is that the signals on the electrodes 12A, 12B, 12C, 12D, etc. are relatively weak. Because of this, if the pre-amplifier 14 were displaced by any significant distance from the electrodes 12A, 12B, 12C, 12D, etc., noise generated in the leads extending from the electrodes would be so large that it would obfuscate the signals from the electrodes. The post amplifier 16 may be displaced by some distance from the electrodes 12A, 12B, 12C, etc. and the pre-amplifier 14 as shown in FIG. 2 because the signals introduced to the post-amplifier are relatively strong.

The electrodes 12A, 12B, 12C, 12D, etc. are preferably connected in pairs. For example, the electrode 12A may provide a signal indicating the brainwave at a first particular position on the patient's head 10 and the electrode 12B may provide a reference signal. Preferably the electrodes 12A and 12B are physically disposed close to each other on the patient's head to minimize any differences in the noise on the electrodes. The electrodes 12C and 12D may also be paired, preferably in close physical relationship to each other, with the electrode 12C disposed at a selected position to indicate the brainwave at that position and the electrode 12D disposed to provide a reference position.

The circuitry in the pre-amplifier 14 (FIG. 3) may include a low pass filter and protection circuit generally indicated at 18, a differential amplifier generally indicated at 20 and a high pass-filter generally indicated at 22. Each of the stages 18, 20 and 22 is defined by a box of broken lines, the boxes being respectively designated as 18, 20 and 22. The circuit 18 includes a terminal 24 for reproducing a signal representing the brainwaves at the electrode 12A and includes a terminal 26 for reproducing the reference signal at the electrode 12B.

The signals at the terminals 24 and 26 are respectively introduced to an RC filtering circuit defined by a resistor 28 and a capacitor 30 in series between the terminal 24 and a reference such as a ground 32. In like manner, the signals at the terminal 26 are introduced to an RC filtering circuit defined by a resistor 34 and a capacitor 36 in series between the terminal 26 and the reference such as the ground 32. A capacitor 38 is connected between the ungrounded terminals of the capacitor 30 and the capacitor 36.

A diode 40 is electrically disposed between the undergrounded terminal of the capacitor 30 and the reference such as the ground 32, and a diode 42 is electrically disposed between the ungrounded terminal of the capacitor 36 and the reference such as the ground 32. A resistor 43 extends electrically between the ungrounded terminal of the capacitor 30 and a first input terminal in the differential amplifier 20. In like manner, a resistor 45 extends electrically between the ungrounded terminal of the capacitor 36 and a second input terminal of the differential amplifier 20.

The amplifier 20 may be an INA102 amplifier manufactured by Burr Brown in Phoenix, Ariz. The amplifier has near its external periphery numbers individually designating the different pins in the amplifier. The pins are provided with "B" suffices to distinguish them from other components in the drawings. The output terminal of the differential amplifier 20 is common with one terminal of a capacitor 44, the other terminal of which has a connection to an ungrounded terminal of a resistor 46. An output line 48 extends from the output terminal of the resistor 46. The capacitor 44 and the resistor 46 are included in the high pass filter 22.

The signals produced at the electrodes such as the electrodes 12A and 12C have different frequency ranges dependent upon the location of such electrodes on the head. However, the different frequency ranges have maximum frequencies less than approximately one hundred hertz (100 Hz). The RC circuit defined by the resistor 28 and the capacitor 30 operates to pass signals from the terminal 24 at frequencies less than approximately one hundred (100 Hz) and to bypass signals above this approximate frequency to ground. The RC circuit defined by the resistor 34 and the capacitor 36 provides a similar filtering action on the signals from the terminal 26. The diodes 40 and 42 respectively pass to ground the negative portions of the signals below approximately one hundred hertz (100 Hz).

The differential amplifier 20 compares the wave shapes of the signals passing to the amplifier through the resistors 44 and 46 and produces an output signal constituting the difference between the wave shape of the signal from the terminal 24 relative to the signal from the terminal 26. This constitutes the portion of the signal from the terminal 24 that is different from the signal on the terminal 26. The differential amplifier 20 is constructed to provide a balanced operation of this common mode rejection even though the impedances of the signals on its input terminals are not equal. The signals from the differential amplifier 20 then pass to the high pass filter 22 which eliminates the DC component of the signal introduced to it.

The signals from the pre-amplifier 14 are introduced to the post-amplifier 16 (FIGS. 4A–4D). As shown in FIG. 2, the post amplifier 16 may be displaced from the pre-amplifier 14 because the signals on the electrodes such as the electrode 12A have been amplified by the pre-amplifier and are now relatively strong. Some of the stages in the post-amplifier 16 are shown in block form because they may be considered to be conventional. Other stages are shown in some detail because they contribute to the advantages of the post-amplifier 16 over the prior art.

FIG. 4 shows the relative layouts of the portions of the post-amplifier 16 as shown in FIGS. 4A–4D. The post-amplifier 16 includes a buffer 50 (FIG. 4A) which may be connected to the line 48 (also shown in FIG. 3) and which may be conventional. Because of this, the buffer 50 is shown in block form. The buffer 50 preserves the frequency characteristics of the high pass filter 22 in the pre-amplifier 14. The output signals from the buffer 50 pass to an isolation amplifier generally indicated at 54 and enclosed within a broken rectangle.

The isolation amplifier 54 includes as its primary element an optical coupler 56 which is designated by Burr-Brown as an ISO-100 coupler. This coupler has the advantage of providing an optical coupling between the output signal from the buffer 50 and an input signal to an amplifier 58 which is also supplied by Burr-Brown and which may be considered as a part of the optical coupler. The coupler 56 and the amplifier 58 preserve the signal characteristics of the output signal from the buffer 50 from a linearity standpoint while providing a ground in the coupler independent of the ground in the buffer 50. In effect, the optical coupler 56 and the amplifier 58 effectively isolate the post-amplifier 16 from the pre-amplifier 14.

As will be seen in FIGS. 4A–4E, the optical coupler 56 and the amplifier 58 and other stages in the post-amplifier 50 have a plurality of pins or terminals. These pins or terminals are designated by numerals. For example, the optical coupler 56 has two (2) pins or input terminals which are respectively designated as "15c" and "12c". The numerical designations of these pins or terminals correspond to the numerical designations provided by Burr-Brown for these pins or terminals. However, the pins in the optical coupler 56 have a suffix "c" to distinguish them from other components and from pins in other stages. The output from the amplifier 58 passes through a line 59 in FIGS. 4A and 4B to an amplifier 60 (FIG. 4B) which may be constructed in a conventional manner and which is accordingly shown in block form.

The output from the amplifier 60 is introduced to a low pass filter generally indicated at in FIG. 3 62. The low pass filter 62 includes a filter stage 64 which may be designated as a 1060A filter by Linear Technology. As with other stages in the post-amplifier 16, the filter 64 includes a number of terminals which have numerical designations corresponding to those used by Burr-Brown. The terminals in the filter 64 have a "d" suffix to distinguish them from other components and from terminals in other stages. These terminals include terminals designated as "10d" and "11d". The terminals 10d and 11d in the filter 64 receive clock signals on a line 66 (FIGS. 4A and 4B) from a clock source indicated at a terminal 68 (FIG. 4A). The clock signals have a frequency which limit the upper frequency range of the signals passed by the filter 64 in FIG. 4B.

As previously discussed, each of the electrodes 12A, 12B, 12C, 12D, etc., in FIG. 1 produces signals within a frequency range to approximately one hundred hertz (100 Hz). However, for each individual one of the electrodes such as the electrode 12A or the electrode 12C, the investigator is interested in only a particular portion of the maximum frequency range of approximately one hundred hertz (100 Hz). The limited frequency range of interest to the investigator at each electrode is dependent upon the position of the electrode on the patient's head. For example, the signals at the electrode 12A may have a frequency range of approximately sixty hertz (60 Hz) and the frequency range of the signals at the electrode 12C may be approximately seventy hertz (70 Hz). Since the post-amplifier 16 is operating on the signals at the electrode 12A when the frequency range of these signals is approximately sixty hertz (60 Hz), the clock signal on the line 66 has a frequency of approximately sixty hertz (60 Hz) in accordance with the example given above.

The cut-off characteristics of the signals from the filter 64 may be varied. For example, the signals from the filter 64 may be provided with sharp characteristics as indicated at 70 in FIG. 6. Alternatively, the cut-off characteristics may be relatively shallow or gradual as indicated at 72 in FIG. 6. The cut-off characteristics of the signal from the filter 64 may be varied by varying the values of the resistors connected to the filter 64. These include resistors 74a, 74b, 74c, 74d, 74e, 74f and 74g.

The signals from the filter 64 pass through the terminal 18 in the filter and a line 75 (FIGS. 4B and 4C) to a high pass filter generally indicated at 76 in FIG. 4(C). The high pass filter 76 may be a filter designated MF6-100 by National Semiconductor or Linear Technology. The filter 76 is provided with a plurality of terminals which have designations corresponding to the designation provided by the manufacturer. However, the terminal designations are followed by the suffix "e" to distinguish such terminal designations from the designations of other components and from the terminal designations of other stages.

The filter 76 also receives a clock signal on a line 78 from a clock source indicated at a terminal 80 in FIG. 4A. This clock signal controls the frequencies which are filtered by the filter 76 in FIG. 4(C) at the low end of the frequency range introduced by the filter 64 in FIG. 4(B) to the filter 76. For example, the frequency of the clock signal at the terminal 80 may be such that the filter 76 passes signals only at frequencies above approximately two hertz (2 Hz). The frequency range of the signals passing to a high pass filter 82 from the filter 76 may accordingly be between approximately two hertz (2 Hz) and sixty hertz (60 Hz) in the example given above.

The output from the pin or terminal 3e in the filter 76 in FIG. 4(C) passes through a line 80 to a high pass filter 82. The filter 82 may be constructed in a conventional manner. Because of this, it is shown in block form. It reconstitutes sine signals after the operation of the filter 76. The output from the filter 82 passes to a high pass filter 84 which may also be constructed in a conventional manner. The filter 84 is accordingly shown in block form. The filter 84 is also instrumental in converting the signals from the filter 76 to sine wave signals. The signals then pass through a line 85 to a buffer 86 in FIG. 4(D). The buffer 86 operates to reduce the impedance of the signals introduced to the buffer and to pass the low impedance signals to a driver generally indicated at 88. The buffer 86 may be conventional and is accordingly shown in block form.

The driver 88 has a first lead 90 which provides an output signal when the output signal is not being recorded in a recorder 92. The driver 88 also includes an amplifier 91 which introduces signals to the central conductor in a coaxial cable generally indicated at 94. The central connector of the coaxial cable 94 is connected to the recorder 92 which records the signals produced on the electrode 12A in FIG. 1. The signals are recorded with fidelity in the recorder 92 because of the low impedance provided by the buffer 86.

Just as the investigator is interested in only a first particular range of frequencies (e.g. 60 Hz) in the brain waves generated at the position of the electrode 12A, the investigator is interested in only a second particular range of frequencies (e.g. 70 Hz) in the brain waves generated at the position of the electrode 12C. Similarly, just as the electrode 12B provides a reference signal for the signal on the electrode 12A, the electrode 12D provides a reference signal for the signal on the electrode 12C. The electrodes in each pair (e.g. the electrodes 12A and 12B) are preferably disposed close to each other but this may not be necessary in all instances.

Pairing pairs of electrodes, one electrode in the pair to provide an information signal and the other electrode in the pair to provide a reference signal, is desirable in order to assure that there will not be crosstalk between the different ones of the electrodes providing the information signals. This pairing is in contrast to the systems of the prior art where one reference electrode provides a reference for a plurality of electrodes producing information signals. In the systems of the prior art, cross talk tends to occur through the reference electrode between different electrodes providing information signals. This crosstalk is particularly undesirable because the signals representing brain wave information as at the electrodes 12A and 12C have very low amplitudes such that the crosstalk constitutes noise which obscures the information in the information signals.

As will be appreciated, the pre-amplifier 14 provides a pre-amplification of the signals on the electrode 12A. A substantially identical pre-amplifier is provided for the electrode 12C. The output signals from the substantially identical pre-amplifier for the electrode 12C are introduced to a post-amplifier generally indicated at 98 in FIG. 4(E). The post-amplifier 98 has a construction substantially identical to the post-amplifier 16. Because of this, only portions of the post-amplifier 98 are shown in FIG. 4 (E).

The post-amplifier 98 in FIG. 4(E) includes a low-pass filter generally indicated at 100 and corresponding to the filter 62 in FIG. 4(B). The clock signal on the line 66 is introduced to a stage 101 in the low-pass filter 100 in FIG. 4(B) in a manner similar to the introduction of this clock signal to the stage 64 in the filter 62 in FIG. 4(B). Similarly, the post-amplifier 16 has a high pass filter generally indicated at 102 in FIG. 4(E). This filter is substantially identical to the high pass filter 76 in FIG. 4(C) in the post-amplifier 16. Clock signals on the line 78 are introduced to the high pass filter 102 in FIG. 4(E) in a manner similar to the introduction of the clock signals on the line 78 to the high pass filter 76 in FIG. 4(C).

The terminals in the low pass filter 100 are provided with a suffix "f" and the terminals in the high pass filter 102 are provided with a suffix "g". In this way, the terminals in the filters 100 and 102 are distinguished from other components and the terminals in other stages. In order to accommodate to the different frequency ranges of the signals on the electrodes 12A and 12C, the clock signals on the terminals 68 and 80 may be swept progressively through a range of frequencies. For example, the clock signals on the terminal 68 may be swept through a range of frequencies between approximately forty hertz (40 Hz) and one hundred hertz (100 Hz) to accommodate for the individual frequency ranges of the signals at the different electrodes such as the electrodes 12A and 12C. In this way, optimal outputs are provided in the post-amplifier 16 for the signals at the electrode 12A and in the post-amplifier 98 for the signals at the electrode 12C.

FIG. 5 provides a block diagram of a system for providing a sweep of frequencies for the clock signals on the terminal 68 and for introducing such clock signals at each instant through the line 66 to the filter 62 in the post-amplifier 16 and to the corresponding filter 100 in the post-amplifier 98. Such a system is shown in block form because sweep circuits are conventional in the prior art. Similar frequency sweeps may be provided for the low frequencies through the line 78 to the high pass filter 76 in the post-amplifier 16 and to the high pass filter 102 in the post-amplifier 98.

The signals produced at other electrodes in FIGS. 1 and 2 than the electrodes 12A–12D may result from movements of the patient's eyes. A post-amplifier generally indicated at 106 in FIGS. 7A–7D may be provided to detect movements of the patient's eyes and to provide electrooculograms of such eye movements. A map is shown in FIG. 7 to indicate the sequence in FIGS. 7A–7C of the post-amplifier 106. The post-amplifier 106 may include an electrode 108A (FIG. 7D) which is connected to the patient's head near the patient's eyes and may also include an electrode 108B for providing a reference.

The post-amplifier 106 does not have to include a pre-amplifier corresponding to the pre-amplifier 14 because the signals from the patient's eyes are relatively strong. Furthermore, the post-amplifier 106 may be displaced from the electrodes 108A and 108B (FIG. 7D) because of the strength of the signals at these electrodes. Instead, the post-amplifier 106 may include a low pass filter 112 and a differential amplifier 114. The low pass filter 112 and the differential amplifier 114 may be constructed in a conventional manner. The output of the differential amplifier 114 may be introduced to a high pass filter 116 which may also be constructed in a conventional manner. As will be appreciated, the low pass filter 112, the differential amplifier 114 and the high pass filter 116 may be respectively considered to correspond to the low pass filter 18, the differential amplifier 20 and the high pass filter 22 in the pre-amplifier 14 of FIG. 3.

The output of the high pass amplifier in FIG. 7A is introduced to a buffer 140. An isolation amplifier 142 receives the output of the buffer 142. The output of the isolation amplifier 142 passes through a line 143 in FIGS. 7A and 7B to a high pass filter 144 in FIG. 7B. The output from the high pass filter 144 in turn passes to a high pass filter 146. The output from the high pass 146 in turn passes to a buffer 148. The buffer 148 in turn passes signals through a line 149 in FIGS. 7B and 7C to a driver generally indicated at 150 in FIG. 7C. The driver 150 corresponds to the driver 88 in FIG. 4D.

As will be seen from a circuitry comparison, the circuitry shown in FIGS. 7A–7C is substantially identical, with certain minor exceptions, to the circuitry shown in FIGS. 4A–4D. The gain of the circuitry shown in FIG. 7 may be different from the circuitry shown in FIG. 4 because the signal at the electrode 108A is stronger than the signal at the electrode 12A. The frequency band of the post-amplifier 106 may also be different from the frequency band of the post-amplifier 16. For example, the frequency band of the post-amplifier 106 may be approximately forty hertz (40 Hz) as distinguished from a frequency band of approximately one hundred hertz (100 Hz) for the post-amplifier 16.

The system providing electrooculograms may include a second post-amplifier corresponding to the post-amplifier 106. This post-amplifier is generally indicated at 118 in FIGS. 7(D) and 7(E). The post-amplifier 118 may respond to information signals at an electrode 108C and reference signals at an electrode 108D. The post-amplifier 118 may include stages having the same designation as the stages in the post-amplifier 106 except that they are followed by the suffix "A". The post amplifier 118 includes a driver (not shown) corresponding to the driver 150 in FIG. 7C.

The operation of the post-amplifiers 106 and 118 may be controlled with respect to the frequency ranges of these post-amplifiers by the frequencies of clock signals on terminals 120 (FIG. 7(F)) and 122 (FIG. 7(G)). The clock signals on the terminal 120 pass through a line 121 to control the operation of the low pass filter 112 in the post-amplifier 106 and the operation of the low pass filter 124 in the post amplifier 112A in the post amplifier 118. These clock signals correspond to the clock signals on the line 68 in FIGS. 4A–4D. As will be seen, the construction of the low pass filters 112 and 112A corresponds to the construction of the low pass filter 62 in FIG. 4(B). The different terminals in the low pass filters 112 and 112A are respectively provided with suffices "h" and "i" to distinguish them from other components and from terminals in other stages.

In like manner, the clock signals on the terminal 122 in FIG. 7(G) pass through a line 127 to control the operation of a high pass filter 116 in the post- amplifier 106 and to control the operation of the high pass filter 116A in the post-amplifier 118. These clock signals correspond to the clock signals on the line 78 in the post-amplifier 16. As will be seen, the construction of the high pass filters 116 and 116A corresponds to the construction of the high pass filter 76 in FIG. 4(C). The different terminals on the low pass filter 124 and on the high pass filter 126 are respectively provided with suffices "j" and "k" to distinguish them from other components and from terminals in other stages.

The signals provided by the post-amplifiers 16 and 106 may be recorded in a recorder 131 (FIG. 8) in a side-by-side relationship in a synchronous time relationship as shown in FIG. 8. The signals provided by the post amplifiers 98 and 118 may also be recorded side-by-side simultaneously in a synchronous time relationship. A comparison may be made between the side-by-side signals to determine whether the signals at the electrode 12A result from movements of the eye rather than from brain waves at the electrode 108A. A similar determination may be made for the signals from the electrodes 12B and 108B.

The post-amplifier shown in FIGS. 7A–7C and the post-amplifier shown in FIGS. 7(D) and 7(E) may be also used to obtain electrocardiograms. The signals representing the electrocardiograms at the terminals 108a and 108c may be respectively recorded in side-by-side relationship synchronously with the signals in the post-amplifiers 16 and 98 to determine if there is any relationship between the signals representing the patient's brain waves and the signals produced at the patient's heart.

The system and method described above have several distinct advantages over the prior art. The system and method pair electrodes (e.g. 12A and 12B) on a person's head to obtain signals representing the brainwaves at one of the electrodes in the pair. These signals are introduced to the pre-amplifier 14 disposed in juxtaposition to the electrodes 12A and 12B to minimize noise in the pre-amplifier. The pre-amplifier 14 provides a balanced operation in amplifying the differential signals even when the impedance of the electrodes is significantly different.

The post-amplifier 16 may be disposed in displaced relationship to the pre-amplifier 14. The post-amplifier 16 isolates the signals in the post-amplifier electrically from the signals in the pre-amplifier 14 and establishes an independent electrical ground for the signals in the post-amplifier. The post amplifier 16 then provides an amplification in accordance with the individual range of frequencies at each individual one of the electrodes.

The system compares the electroencephalogram signals at the electrodes such as the electrode 12A with the signals representing the electrooculograms such as at the electrode 108a. In this way, the system is able to distinguish the electroencephalogram signals from the electrooculogram signals. A similar distinction can be made between the electroencephalogram signals and electrocardiogram signals.

Although this invention has been disclosed and illustrated with reference to particular embodiments, the principles involved are susceptible for use in numerous other embodiments which will be apparent to persons skilled in the art. The invention is, therefore, to be limited only as indicated by the scope of the appended claims.

I claim:

1. In combination for obtaining a person's electrocardiogram, comprising:
   an electrode constructed to be disposed at a particular position on the head of the person's head to produce signals at such electrode in accordance with the brainwaves at such position,
   a lead extending from the electrode,
   pre-amplifier means disposed in juxtaposition to the electrode and connected to the lead and constructed to provide an output signal amplifying the signal at the electrode and to eliminate noise from such signal,
   amplifier means responsive to the output signal from the pre-amplifier means for amplifying such signal,
   the electrode constituting a first electrode,
   a second electrode constructed to be disposed on the patient's head,
   a third electrode constructed to be disposed on the patient's head and paired with the first electrode, the first electrode providing an information signal and the third electrode providing a reference signal,
   the pre-amplifier means including first means responsive to the information signal from the first electrode and the reference signal applied from the third electrode for representing information in the brain waves at the position of the first electrode,
   a fourth electrode constructed to be disposed on the patient's head and paired with the second electrode, the second electrode providing an information signal and the fourth electrode providing a reference signal,
   the pre-amplifier means including second means responsive to the information signal from the second electrode and the reference signal applied from the fourth electrode for passing only the portion of the information signal representing information in the brain waves at the position of the second electrode.

2. In a combination as set forth in claim 1,
   the pre-amplifier means including a differential amplifier for passing a signal representing only the difference between the information signal and the reference signal.

3. In a combination as set forth in claim 2, means responsive in the pre-amplifier means to the signal passing from the differential amplifier for preventing the passage of any DC components in such signal.

4. In combination for obtaining a patient's electroencephalogram, comprising:

a plurality of electrodes constructed to be disposed at particular positions on the patient's head to produce signals at such electrodes in accordance with the brainwaves at such positions, the electrodes being disposed in pairs with one electrode in each pair providing an information signal and the other electrode in each pair providing a reference signal, the reference electrode in each pair being different from the reference electrode in the other pairs, first means responsive to the information signal and the reference signal in each of the pairs for providing a balanced operation in passing the portion of the information signal representing the brain wave information for such pair only in a first particular range of frequencies, second means responsive to the signal passed by the first means for the electrodes in each pair for passing only the portion of the information signal different from the reference signal for such pair, and third means responsive to the signal from the second means for each pair of electrodes for passing only the portion of such signal above a particular frequency for such pair.

5. In a combination as set forth in claim 4, the first, second and third means being included in a pre-amplifier and the pre-amplifier being juxtaposed to the electrodes in the plurality.

6. In a combination as set forth in claim 5, fourth means disposed at a position displaced from the pre-amplifier for amplifying the signal from the third means in the pre-amplifier, and fifth means for isolating the fourth means from the third means to preserve at the fourth means the characteristics of the signal from the third means.

7. In combination for obtaining an electroencephalogram of a person, comprising:

a plurality of electrodes constructed to be disposed at particular positions on the person's head for producing signals representing the brainwaves of the person at such electrodes, pre-amplifier means constructed to be disposed on the patient's head and connected to the electrodes and juxtaposed to the electrodes for producing a pre-amplification of the signals at the electrodes, means disposed in the pre-amplifier means and responsive to the signals at the electrodes for passing substantially only the signals representing the brain waves of the patient, and post-amplifier means displaced from the pre-amplifier means and operatively coupled to the pre-amplifier means for amplifying the signals from the pre-amplifier means, the pre-amplifier means including means for passing and pre-amplifying the signals from the electrodes substantially only in a range of frequencies between a pre-selected minimal value and a pre-selected maximal value, the electrodes being disposed in pairs, one electrode in each pair providing an information signal and the other electrode in each pair providing a reference signal, the reference electrode in each pair being different from the reference electrode in the other pairs, the pre-amplifier means being operative to pass only the brainwave information in each pair of electrodes.

8. In a combination as set forth in claim 7, the post-amplifier means having an input, the post-amplifier means including means for isolating the signals produced by the pre-amplifier means from the input to the post-amplifier means to preserve in the post-amplifier means the characteristics of the signals produced in the pre-amplifier means.

9. In a combination as set forth in claim 7, the pre-amplifier means including means for establishing a ground for the pre-amplifier means, the post-amplifier means including means for establishing a ground for the post-amplifier means independent of the ground for the pre-amplifier means.

10. In combination for obtaining an electroencephalogram of a person, comprising:

a plurality of electrodes constructed to be disposed at particular positions on the person's head for producing signals representing the brainwaves of the person at such electrodes, pre-amplifier means connected to the electrodes and juxtaposed to the electrodes for producing a pre-amplification of the signals at the electrodes, means disposed in the pre-amplifier means and responsive to the signals at the electrodes for passing substantially only the signals representing the brain waves of the patient, and post-amplifier means displaced from the pre-amplifier means and operatively coupled to the pre-amplifier means for amplifying the signals from the pre-amplifier means, the post-amplifier means including means for providing signals in individual frequency ranges for the signals from different ones of the electrodes in accordance with the frequency range of the brainwave signals at such different ones of such electrodes.

11. In combination for obtaining an electroencephalogram of a person, comprising;

a plurality of electrodes constructed to be disposed at particular positions on the person's head for producing signals representing the brainwaves of the person at the electrodes, the electrodes being paired, a first one of the electrodes in each pair providing signals representing brain wave information and a second one of the electrodes in each pair providing a reference, the reference electrode in each pair being different from the reference electrode in the other pairs, pre-amplifier means constructed to be disposed on the patient's head and operatively coupled to the electrodes in each pair for passing in a particular range of frequencies only the signals representing the brainwaves of the person at the first one of the electrodes in each pair, and post-amplifier means responsive to the signals passed by the pre-amplifier means in the particular range of frequencies for limiting the individual ranges of frequencies for the signals from the different ones of the first electrodes in the pairs in accordance with the frequency characteristics of the brainwaves of the person at such different ones of the first electrodes in the pairs.

12. In a combination as set forth in claim 11, the pre-amplifier means including means for passing the signals from the different ones of the first electrodes in the pairs in the particular range of frequencies collectively for such electrodes, the pre-amplifier means being constructed to provide a balanced operation on the signals from the electrodes in each pair, and the post-amplifier means being responsive to the signals passed by the pre-amplifier means in the particular range of frequencies collectively for the first electrodes in the pairs for passing the signals only in the individual ranges of frequencies within such particular range for the different electrodes in the plurality in accordance with the characteristics of the brainwaves at such different ones of the first electrodes in the pairs.

13. In a combination as set forth in claim 12, means in the pre-amplifier means for establishing a first ground for the pre-amplifier means, and means in the post-amplifier means for establishing for the post-amplifier means a second ground independent of the first ground.

14. In a combination as set forth in claim 11, means in the pre-amplifier means for establishing a first ground for the pre-amplifier means, and means in the post-amplifier means for establishing for the post-amplifier means a second ground independent of the first ground.

15. In combination for obtaining an encephalogram of a person, a plurality of electrodes constructed to be disposed at particular positions on the person's head for producing signals representing the brain waves of the person at such electrodes, pre-amplifier means constructed to be disposed on the patient's head in juxtaposition to the electrodes and connected to the electrodes for passing in a particular range of frequencies the signals produced at the electrodes in representation of the brainwaves of the person, and post-amplifier means for amplifying the signals from the pre-amplifier means, and first means in the post-amplifier means for limiting the range of frequencies in the signals in the post-amplifier means for each individual one of the electrodes in accordance with the frequency characteristics of the brain waves at such individual one of the electrodes to provide an optimal amplification by the post-amplifier means of the signals at such individual one of the electrodes.

16. In combination for obtaining an electroencephalogram of a person, comprising:

A plurality of electrodes constructed to be disposed at particular positions on the persons's head for producing signals representing the brain waves of the person at such electrodes, pre-amplifier means connected to the electrodes for passing in a particular range of frequencies the signals produced at the electrodes in representation of the brainwaves of the person, post-amplifier means for amplifying the signals from the pre-amplifier means, and first means in the post-amplifier means for limiting the range of frequencies of the signals in the post-amplifier means for each individual one of the electrodes in accordance with the frequency characteristics of the brain waves at such individual one of the electrodes to provide an optimal amplification by the post-amplifier means of the signals at such individual one of the electrodes, the electrodes in the plurality being paired to provide signals, at a first one of the electrodes in each pair, representing the brainwaves at such first one of the electrodes and to provide reference signals at a second one of the electrodes in such pair, and the pre-amplifier means being responsive to the signals produced at the first and second electrodes in each pair to pass only the portion of the signals at the first one of electrodes in such pair different from the signals at the second one of the electrodes in such pair.

17. In a combination as set forth in claim 16, second means in the post-amplifier means for isolating the post-amplifier means from the pre-amplifier means, the first means in the post-amplifier means limiting the signals from the first one of the electrodes in each of the different pairs to an individual range of frequencies in accordance with the range of frequencies in the brainwaves of the person at such first one of the electrodes, the pre-amplifier means constructed to be disposed on the person's head in juxtaposition to the electrodes.

18. In a combination as set forth in claim 17, the second means constituting optical means for isolating the post-amplifier means from the pre-amplifier means.

19. In combination for obtaining an electroencephalogram of a person, comprising:

a plurality of electrodes constructed to be disposed at particular positions on the person's head for producing signals representing the brain waves of the person at such electrodes, pre-amplifier means constructed to be disposed on the person's head and connected to the electrodes for passing in a particular range of frequencies the signals produced at the electrodes in representation of the brainwaves of the person, post-amplifier means for amplifying the signals from the pre-amplifier means, and first means in the post-amplifier means for limiting the frequency range of the signals in the post-amplifier means for each individual one of the electrodes in accordance with the frequency characteristics of the brainwaves at such individual one of the electrodes to provide an optimal amplification by the post-amplifier means of the signals at such individual one of the electrodes, and second means in the post-amplifier means for isolating the post-amplifier means from the pre-amplifier means.

20. In combination for obtaining an electroencephalogram of a person, comprising:

a plurality of electrodes constructed to be disposed at particular positions on the person's head for producing signals representing the brain waves of the person at such electrodes, pre-amplifier means connected to the electrodes for passing in a particular frequency range the signals produced at the electrodes in representation of the brain waves of the person, post-amplifier means for amplifying the signals from the pre-amplifier means, and first means in the post-amplifier means for establishing frequency characteristics in the post-amplifier means for each individual one of the electrodes in accordance with the frequency characteristics of the brain waves at such individual one of the electrodes to provide an optimal amplification by the post-amplifier means of the signals at such individual one of the electrodes, the first means in the post-amplifier means providing an individual range of frequencies for the signals from each of the different electrodes only in accordance with the individual range of frequencies at such electrodes in the brainwaves of such person.

21. In combination for obtaining a person's electroencephalogram, comprising;

a plurality of electrodes constructed to be disposed at particular positions on the persons's head to produce signals at such electrodes in accordance with the brainwaves of such person at such positions, means for amplifying the signals at the electrodes, low pass filter means operatively coupled to the amplifying means to pass the signals from the amplifying means, the signals at each of the electrodes having an individual range of frequencies in accordance with the positioning of such electrode on the patient's head, and means for varying the range of frequency response of the low pass filter means at progressive instants of time to determine the characteristics of the signals at such individual ones of the electrodes in accordance with the frequency range of the waveforms at such individual one of the electrodes.

22. In a combination as set forth in claim 21, the low pass filter means having, at the upper end of the range of frequency response, a cut off where the amplitude response to the signals passing through the low pass filter means decreases with progressive increases in frequency, and means for varying the cut off response of the low pass filter means.

23. In a combination as set forth in claim 21, the amplifying means including pre-amplifier means disposed in juxtaposed relationship to the electrodes for providing a pre-amplification of the signals from the electrodes and including post-amplifier means displaced from the electrodes and the pre-amplifier means and responsive to the signals from the pre-amplifying means for amplifying such signals.

24. In a combination as set forth in claim 23, the electrodes in the plurality being connected in pairs to the pre-amplifying means, a first one of the electrodes in each pair providing the signal indicating the brain waveform at the position of such electrode and the other electrode in each pair providing a reference signal, the pre-amplifying means being responsive to the signals from the electrodes in each pair to pre-amplify the portion of the signal from the first one of the electrodes in each pair that is different from the reference signal produced by the other one of the electrodes in such pair.

25. In a combination as set forth in claim 23, means in the amplifier means for isolating the pre-amplifier means from the post-amplifier means while preserving the characteristics in the post-amplifier means of the signals from the pre-amplifier means.

26. In a combination as set forth in claim 23, the pre-amplifier means having a ground, means in the post-amplifier means for passing through the post-amplifier means the characteristics of the signals in the pre-amplifier means and for providing a ground in the post-amplifier means independent of the ground in the pre-amplifier means, the low pass filter means having, at the upper end of the range of frequency response, a cut off where the amplitude response to the signals passing through the low pass filter means decreases with progressive increases in frequency, and means for varying the cut off response of the low pass filter means, the electrodes being connected in pairs to the pre-amplifying means, a first one of the electrodes in each pair providing the signal indicating %he brain waveform at the position of such electrode and the other electrode in such pair providing a reference signal, the reference electrode in each pair being different from the reference electrode in the other pairs, the pre-amplifying means being responsive to the signals from the electrodes in each pair to pre-amplify the portion of the signal from the first one of the electrodes in each pair that is different from the reference signal from the other one of the electrodes in such pair.

27. In combination for obtaining a person's electroencephalogram, comprising:

first electrodes constructed to be disposed on the person's head for producing first signals indicating the person's brainwaves at the positions of the electrodes and having first impedances, second electrodes constructed to be disposed on the patient's head for producing reference signals and having second impedances different from the first impedances, each of the first electrodes being paired with an individual one of the second electrodes, first means operative in a balanced mode even with the differences in impedances at the first and second electrodes in each pair for providing a pre-amplification of only the portions of the signal from the first electrode in such pair different from the reference signal at the second electrode in such pair, and second means for amplifying the signal from the first means for each pair of electrodes in an electrically isolated relationship to the first means for such pair of electrodes.

28. In a combination as set forth in claim 27, the signal on each of the first electrodes having a particular range of frequencies dependent upon the positioning of such first electrode on the person's head, and third means for amplifying the signal from the second means for each of the first electrodes only in the particular range of frequencies for the signal on such first electrode.

29. In a combination as set forth in claim 27, the first means being disposed in juxtaposed relationship to the first electrode.

30. In a combination as set forth in claim 27, a third electrode constructed to be disposed on the patient's head for producing a third signal indicating the brainwaves of the person at the position of the electrode and having a third impedance, the reference signal constituting a first reference signal, a fourth electrode constructed to be disposed on the patient's head for producing a second reference signal having a fourth impedance different from the third impedance, third means operative in a balanced mode even with the difference in impedance at the third and fourth electrodes for providing a pre-amplification of only the portion of the signal from the third electrode different from the second reference signal, and fourth means for amplifying the signal from the third means in an electrically isolated relationship to the third means.

31. In combination for obtaining a person's electroencephalogram, comprising:

a plurality of electrodes constructed to be disposed in spaced relationship to one another on the person's head, the electrodes being paired to define in each pair a first electrode providing an information signal indicating the brainwave of the person at the position of the first electrode and a second electrode providing a reference signal, the second electrode in each pair being different from the second electrode in the other pairs, a plurality of pre-amplifier means each responsive to the signals from the first and second electrodes in an individual one of the pairs to produce a pre-amplified signal representing the portion of the information signal at the first electrode in the associated pair different from the reference signal at the second electrode in the associated pair, and a plurality of amplifier means each responsive to the signal from an individual one of the pre-amplifier means for amplifying the pre-amplified signal from the individual one of the pre-amplifier means only in an individual range of frequencies dependent upon the position of the first electrode providing in the associated pair the signal of the person's brainwave to the individual one of the pre-amplifier means.

32. In a combination as set forth in claim 31 wherein the plurality of pre-amplifier means are disposed on the person's head in juxtaposed relationship to the electrodes in the plurality.

33. In a combination as set forth in claim 32, comprising:

means responsive in each of the amplifier means to the signal from the associated one of the pre-amplifier means, but in electrically isolated relationship to such pre-amplifier means, to provide a substantially linear amplification of the signal from such pre-amplifier means.

34. In combination for obtaining a person's electroencephalogram, comprising:

a plurality of electrodes constructed to be disposed in spaced relationship to one another on the person's head, the electrodes being paired to define in each pair a first electrode providing an information signal indicating the brainwave of the person at the position of the first electrode and a second electrode providing a reference signal, a plurality of pre-amplifier means each responsive to the signals from the first and second electrodes in an individual one of the pairs to produce a pre-amplified signal representing the portion of the information signal at the first electrode in the associated pair different from the reference signal at the second electrode in the associated pair, a plurality of amplifier means each responsive to the signal from an individual one of the pre-amplifier means for amplifying the pre-amplified signal from the individual one of the pre-amplifier means in an individual range of frequencies dependent upon the position of the first electrode providing in the associated pair the signal of the person's brainwave to the individual one of the pre-amplifier means, and means for providing progressive changes in the frequency range of the signals amplified by the amplifier means in the plurality to obtain an amplification in the signal from each individual one of the amplifier means upon the production of the range of frequencies individual to the signal in such amplifier means.

35. In combination for obtaining a person's electroencephalogram, comprising:

an electrode constructed to be disposed at a particular position on the person's head to produce signals at such electrode in accordance with the brainwaves at such position, a lead extending from the electrode, pre-amplifier means disposed in juxtaposition to the electrode and connected to the lead and constructed to provide an output signal amplifying the signal at the electrode and to eliminate noise from such signal, amplifier means responsive to the output signal from the pre-amplifier means for amplifying such signal, the electrode constituting a first electrode and being constructed to be disposed at a first particular position on the person's head, a second electrode constructed to be disposed at a second particular position on the person's head near the person's eye to produce electroocular signals at such second electrode in accordance with the brainwaves of the person at such position, the amplifier means constituting first amplifier means, and second amplifier means responsive to the signal from the second electrode for amplifying such signal, and means for simultaneously recording the signals from the first and second amplifier means.

36. In a combination as set forth in claim 35, a third electrode paired with the first electrode to provide a first reference signal, a fourth electrode paired with the second electrode to provide a second reference signal, the pre-amplifier means being responsive to the signals on the first and third electrodes to amplify the differences between the signals from the first and third electrodes, and the second amplifier means being responsive to the signals from the second and fourth electrodes to amplify the differences between the signals from the second and fourth electrodes.

37. In combination for obtaining a patient's electroencephalogram, comprising:

a plurality of electrodes constructed to be disposed at particular positions on the patient's head to produce signals at such electrodes in accordance with the brainwaves at such positions, the electrodes being disposed in pairs with one electrode in each pair providing an information signal and the other electrode in each pair providing a reference signal, first means responsive to the information signal and the reference signal in a particular one of the pairs for providing a balanced operation in passing the information signal only in a first particular range of frequencies, second means responsive to the signal passed by the first means for passing only the portion of the information signal different from the reference signal, third means responsive to the signal from the second means for passing only the portion of such signal above a particular frequency, the reference signal constituting a first reference signal, at least a second pair of electrodes constructed to be disposed on the person's head near the person's eyes to produce electrooculogram signals indicating movements of the person's eyes and to produce a second reference signal different from the first reference signal, and fourth means responsive to the signals from the second pair of electrodes for producing the portion of the electroencephalogram signals different from the second reference signal.

38. In a combination as set forth in claim 37, means for simultaneously recording the signals from the third means and the fourth means for purposes of comparison of such signals to eliminate the effects of eye movements from the signals from the third means.

39. In a combination as set forth in claim 38, the pre-amplifier means including means for passing and pre-amplifying the signals from the electrodes substantially only in a range of frequencies between a pre-selected minimal value and a pre-selected maximal value, and the post-amplifier means having an input, the post-amplifier means including means for isolating the signals produced by the pre-amplifier means from the input to the post-amplifier means to preserve in the post-amplifier means the characteristics of the signals produced in the pre-amplifier means, the pre-amplifier means including means for establishing a ground for the pre-amplifier means, the post-amplifier means including means for establishing a ground for the post-amplifier means independent of the ground for the pre-amplifier means.

40. In combination for obtaining an electroencephalogram of a person, comprising:

a plurality of electrodes constructed to be disposed at particular positions on the person's head for producing signals representing the brainwaves of the person at the electrodes, pre-amplifier means operatively coupled to the electrodes for passing in a particular range of frequencies only the signals representing the brainwaves of the person at different ones of the electrodes in the plurality, and post-amplifier means responsive to the signals passed by the pre-amplifier means in the particular range of frequencies for passing the signals in individual ranges of frequencies for the different ones of the electrodes in the plurality in accordance with the characteristics of the brainwaves of the person at such different ones of the electrodes, an additional electrode constructed to be disposed at a particular position on the person's head near the person's eye for producing signals representing the electrooculogram of the person, and amplifier means responsive to the signals from the additional electrode for producing amplifications of such signals.

41. In a combination as set forth in claim 40, means for simultaneously recording the signals from the post-amplifier means and the amplifier means.

42. In a combination as set forth in claim 40, means in the pre-amplifier means for establishing a first ground for the pre-amplifier means, means in the post-amplifier means for establishing for the post-amplifier means a second ground independent of the first ground, and means in the amplifier means for establishing for the amplifier means a third ground independent of the first and second grounds.

43. In a combination as set forth in claim 41, means in the pre-amplifier means for establishing a first ground for the pre-amplifier means, means in the post-amplifier means for establishing for the post-amplifier means a second ground independent of the first ground, and means in the amplifier means for establishing for the amplifier means a third ground independent of the first and second grounds, the pre-amplifier means including means for passing the signals from the different ones of the electrodes in the particular range of frequencies collectively for such electrodes, and the post-amplifier means being responsive to the signals passed by the pre-amplifier means in the particular range of frequencies for passing the signals in the individual ranges of frequencies within such particular range for the different electrodes in accordance with the characteristics of the brainwaves at such different ones of the electrodes.

44. In combination for obtaining an electroencephalogram of a person, comprising:

a plurality of electrodes constructed to be disposed at particular positions on the person's head for producing signals representing the brain waves of the person at such electrodes, pre-amplifier means connected to the electrodes for passing the signals produced at the electrodes in representation of the brain waves of the person, post-amplifier means for amplifying the signals from the pre-amplifier means, first means in the post-amplifier means for establishing characteristics in the post-amplifier means for each individual one of the electrodes in accordance with the characteristics of the brain waves at such individual one of the electrodes to provide an optimal amplification by the post-amplifier means of the signals at such individual one of the electrodes, an additional electrode constructed to be disposed at a particular position on the person's head near the person's eye for producing signals representing the electrooculogram of the person, and amplifier means responsive to the signals from the additional electrode for producing amplifications of such signals.

45. In a combination as set forth in claim 44, means for simultaneously recording the signals from the post-amplifier and the amplifier means.

46. In combination for obtaining an electroencephalogram of a person, comprising:

a plurality of electrodes constructed to be disposed at particular positions on the person's head for producing signals representing the brain waves of the person at such electrodes, pre-amplifier means connected to the electrodes for passing the signals produced at the electrodes in representation of the brainwaves of the person, post-amplifier means for amplifying the signals from the pre-amplifier means, first means in the post-amplifier means for establishing characteristics in the post-amplifier means for each individual one of the electrodes in accordance with the characteristics of the brain waves at such individual one of the electrodes to provide an optimal amplification by the post-amplifier means of the signals at such individual one of the electrodes, second means in the post-amplifier means for isolating the post-amplifier means from the pre-amplifier means, an additional electrode constructed to be disposed at a particular position on the person's head near the person's eye for producing signals representing the electrooculogram of the person, and amplifier means responsive to the signals from the additional electrode for producing an amplification of such signals.

47. In a combination as set forth in claims 46, means for simultaneously recording the signals from the post-amplifier means and the amplifier means, the second means constituting optical means.

48. In combination for obtaining a person's electroencephalogram, comprising;

a plurality of electrodes constructed to be disposed at particular positions on the persons's head to produce signals at such electrodes in accordance with the brainwaves of such person at such positions, means for amplifying the signals at the electrodes, low pass filter means operatively coupled to the amplifying means to pass the signals from the amplifying means, the signals at each of the electrodes having an individual range of frequencies in accordance with the positioning of such electrode on the patient's head, means for varying the range of frequency response of the low pass filter means at progressive instants of time to determine the characteristics of the signals at such individual ones of the electrodes in accordance with the frequency range of the waveforms at such individual one of the electrodes, an additional electrode constructed to be disposed at a particular position on the person's head to produce at such additional electrode signals representing electrooculograms of the movements of the person's eyes, and means for amplifying the signals at the additional electrode, the varying means being operative to vary the response of the additional amplifying means at the progressive instants of time to determine the characteristics of the signals at such individual electrode.

49. In a combination as set forth in claim 48, means for simultaneously recording at each progressive instant of time the signals produced by the amplifying means for the signals at the electrodes and the amplifying means for the signals at the additional electrodes.

50. In a combination as set forth in claim 48, the electrodes in the plurality being connected in pairs to the pre-amplifying means, a first one of the electrodes in each pair providing the signal indicating the brain waveform at the position of such electrode and the other electrode in each pair providing a reference signal, the pre-amplifying means being responsive to the signals from the electrodes in each pair to pre-amplify the portion of the signal from the first one of the electrodes in each pair that is different from the reference signal at the other electrode in such pair.

51. In a combination as set forth in claim 49, a plurality of electrodes constructed to be disposed at particular positions on the person's head to produce signals at such electrodes in accordance with the brainwaves of such person at such positions, means for amplifying the signals at the electrodes, low pass filter means operatively coupled to the amplifying means to pass the signals from the amplifying means, the signals at each of the electrodes having an individual range of frequencies in accordance with the positioning of such electrode on the patient's head, means for varying the range of frequency response of the low pass filter means at progressive instants of time to determine the characteristics of the signals at each individual ones of the electrodes in accordance with the frequency range of the waveforms at such individual one of the electrodes, the additional electrode being paired with a further electrode whereby the further electrode provides a reference signal.

52. In combination for obtaining a person's electroencephalogram, comprising:

a first electrode constructed to be disposed on the person's head for producing a first signal indicating the person's brainwaves at the position of the electrode and having a first impedance, a second electrode constructed to be disposed on the patient's head for producing a reference signal having a second impedance different from the first impedance, first means operative in a balanced mode even with the differences in impedance at the first and second electrodes for providing a pre-amplification of only the portions of the signal from the first electrode different from the reference signal, second means for amplifying the signal from the first means in an electrically isolated relationship to the first means, the signal on the first electrode having a particular range of frequencies dependent upon the positioning of the first electrode on the person's head, third means for amplifying the signal from the second means in the particular range of frequencies, the particular range of frequencies constituting a first particular range, a second electrode constructed to be disposed on the person's head for producing a second signal indicating the movements of the person's eyes, the signal on the second electrode having a second particular range of frequencies dependent upon the positioning of the second electrode, and fourth means for amplifying the signal from the second electrode in the second particular range of frequencies.

* * * * *